United States Patent [19]

Miyahara et al.

[11] Patent Number: 4,733,010

[45] Date of Patent: Mar. 22, 1988

[54] METHOD OF SEPARATING MONOHYDRATE OF L-CYSTEINE HYDROCHLORIDE

[75] Inventors: Shyoichiro Miyahara; Toshiaki Kamiguchi; Tadashi Hashimukai; Kazunari Nitta, all of Fukuoka, Japan

[73] Assignee: Mitsui Toatsu Chemicals, Inc., Tokyo, Japan

[21] Appl. No.: 59,845

[22] Filed: Jun. 9, 1987

[30] Foreign Application Priority Data

Jun. 19, 1986 [JP] Japan ................. 61-141425

[51] Int. Cl.$^4$ ............... C07C 51/487; C07B 57/00
[52] U.S. Cl. ..................... 562/554; 424/72; 562/401; 562/402; 562/557
[58] Field of Search ............. 562/401, 557, 402, 554

[56] References Cited

U.S. PATENT DOCUMENTS

| | | | |
|---|---|---|---|
| 2,178,510 | 10/1939 | Gerber | 562/554 |
| 2,456,742 | 12/1948 | Shabica | 562/401 |
| 2,816,915 | 12/1957 | Gregory | 562/401 |
| 2,898,358 | 8/1959 | Dowling | 562/402 X |
| 3,433,832 | 3/1969 | Swanson et al. | 562/554 |
| 4,613,688 | 9/1986 | Inoue et al. | |

*Primary Examiner*—Werren B. Lone
*Assistant Examiner*—Vera C. Clarke
*Attorney, Agent, or Firm*—Browdy and Neimark

[57] ABSTRACT

Hydrochloric acid is added to a solution containing L-cysteine, L-cystine, L-serine and an inorganic salt until it contains at least 15% by weight of hydrochloric acid. The solution is held at a temperature of at least 20° C. so that the L-cystine and the inorganic salt may form a solid, and the solid is removed from the solution. The solution is cooled to a temperature not exceeding 10° C., so that crystallization may take place to form the monohydrate of L-cysteine hydrochloride. The monohydrate is separated from the L-serine in the solution.

5 Claims, 4 Drawing Figures

METHOD OF SEPARATING MONOHYDRATE OF L-CYSTEINE HYDROCHLORIDE

BACKGROUND OF THE INVENTION

1. Field of the Invention

This invention relates to a method of separating L-cysteine from a solution prepared by the reaction of L-serine. More particularly, it is a method of separating L-cysteine as the monohydrate of its hydrochloride.

L-Cysteine is an unstable compound which is easily oxidized. Therefore, it is usually sold in the form of its hydrochloride. L-Cysteine and its hydrochlorides are mainly used as medicines or materials for medicines, or additives to foods or cosmetics. The use thereof for preparing a cold-wave solution has recently shown a particularly great increase. L-Cysteine is an amino acid containing sulfur.

2. Description of the Prior Art

There are known a variety of methods for producing L-cysteine. They include (1) a method relying upon extraction from a natural substance, (2) a method relying upon organic synthesis, (3) a method relying upon fermentation, and (4) a method using an enzyme. The method relying upon extraction has, however, the disadvantages that there is only an unstable supply of raw materials, and that the extracted product is likely to contain other unnecessary amino acids. The method relying upon fermentation has the disadvantage of being lower in productivity than the method using an enzyme. Therefore, the method using an enzyme is considered to be more advantageous than any other method from the standpoint of industrial application.

There are known a number of methods which synthesize L-cysteine by employing enzymes. They include (1) a method employing cysteine synthetase to synthesize L-cysteine from L-serine and hydrogen sulfide, and (2) a method employing serine sulfhydrase to synthesize L-cysteine from L-serine and hydrogen sulfide, or from β-chloroalanine and hydrogen sulfide. Japanese Patent Application No. 84545/1985 discloses the method which was invented by the inventors of this invention. It employs sulfhydryl synthetase for reacting L-serine and a metal hydrosulfide to produce L-cysteine.

Whichever method may be employed, however, it is very difficult to separate L-cysteine from a solution obtained as a product of reaction, since the solution has a complicated composition, and since L-cysteine is highly soluble in water.

When the method using an enzyme or relying upon fermentation is employed, a large amount of an inorganic salt, such as sodium chloride, is formed when the pH of the solution is controlled during its reaction, or when bacterial impurities are removed from the aqueous reaction product. The product unavoidably contains cystine as a by-product of the reaction. Moreover, it contains the unreacted L-serine which need be collected therefrom, as it is expensive. While it is necessary to refine the reaction product to separate L-cysteine from any such inorganic salt, unreacted L-serine and cystine, it is difficult to separate L-cysteine effectively without causing any appreciable loss thereof, since it has a high degree of solubility in water.

Therefore, there is known a method which oxidizes L-cysteine in the reaction product into L-cystine, which is less soluble in water, instead of separating it directly. The L-cystine thereby formed is separated from the reaction product and converted again to L-cysteine by electrolytic reduction, etc. It is, however, evident that this method is entirely unstable for industrial application from the standpoints of yield, operation and cost.

SUMMARY OF THE INVENTION

Under these circumstances, it is an object of this invention to provide a method which can overcome the drawbacks of the prior art as hereinabove pointed out and which can separate L-cysteine efficiently from a reaction product.

This object is attained by a method of separating L-cysteine from a solution containing L-cysteine, L-cystine, L-serine and an inorganic salt which comprises adding hydrochloric acid to the solution until it contains at least 15% by weight of hydrochloric acid, holding the solution at a temperature of at least 20° C. to separate solids containing the L-cystine and the inorganic salt from the solution, cooling the solution to a temperature not exceeding 10° C. to separate additional solids by crystallization, while leaving the L-serine in the solution to form a monohydrate of L-cysteine hydrochloride, and separating the monohydrate from the solution.

DETAILED DESCRIPTION OF THE INVENTION

As a result of their efforts to obtain an efficient method of separating L-cysteine from a reaction product of L-serine, the inventors of this invention have discovered that the L-cysteine, L-serine, sodium chloride and L-cystine which the reaction product contains are greatly different from one another in their solubility in an aqueous solution containing hydrochloric acid, and that their differences depend on the hydrochloric acid content of the solution and its temperature, as is obvious from FIGS. 1 to 4.

Figure 1:
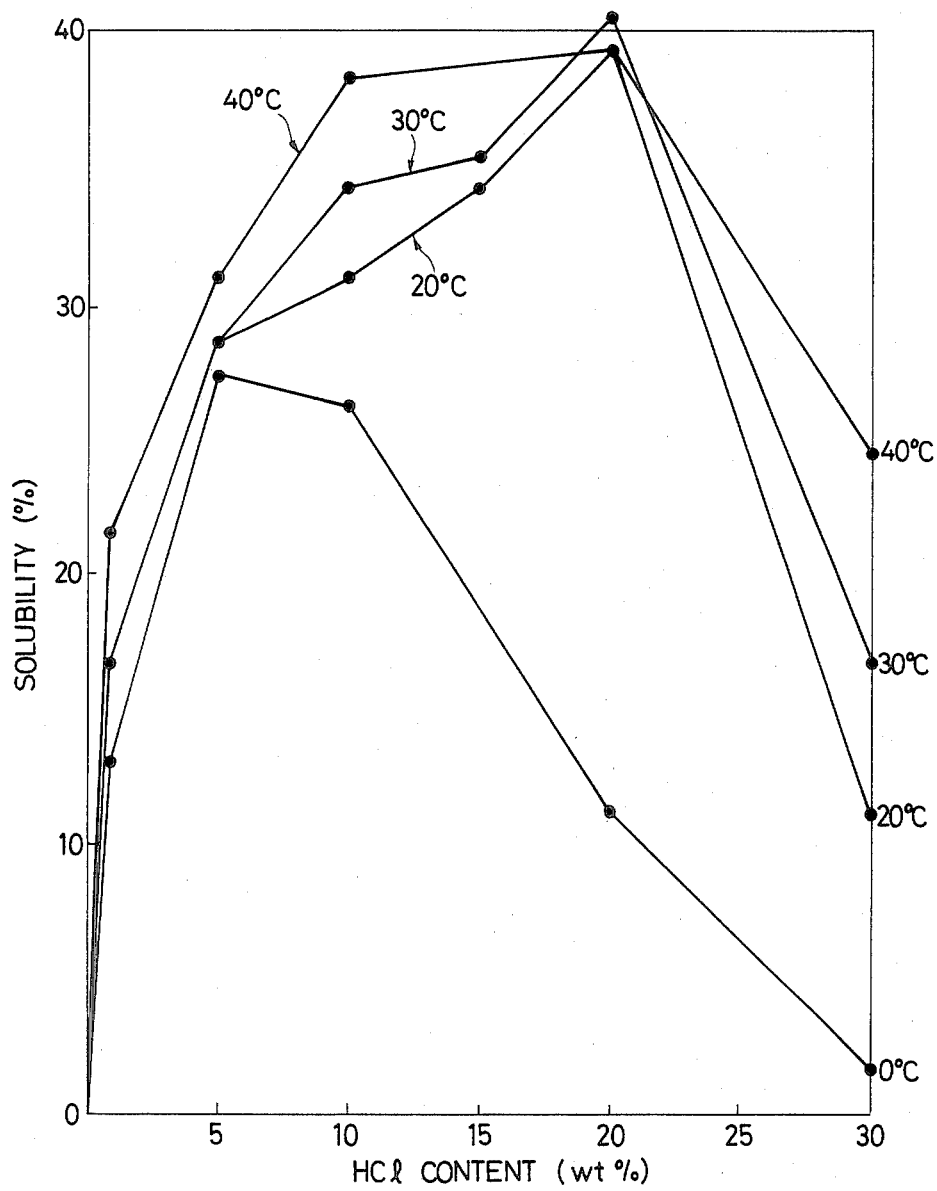
FIG. 1 is a graph showing the solubility of L-cysteine in an aqueous solution in relation to its hydrochloric acid content at temperatures of 0° C., 20° C., 30° C. and 40° C., respectively.
Figure 2:
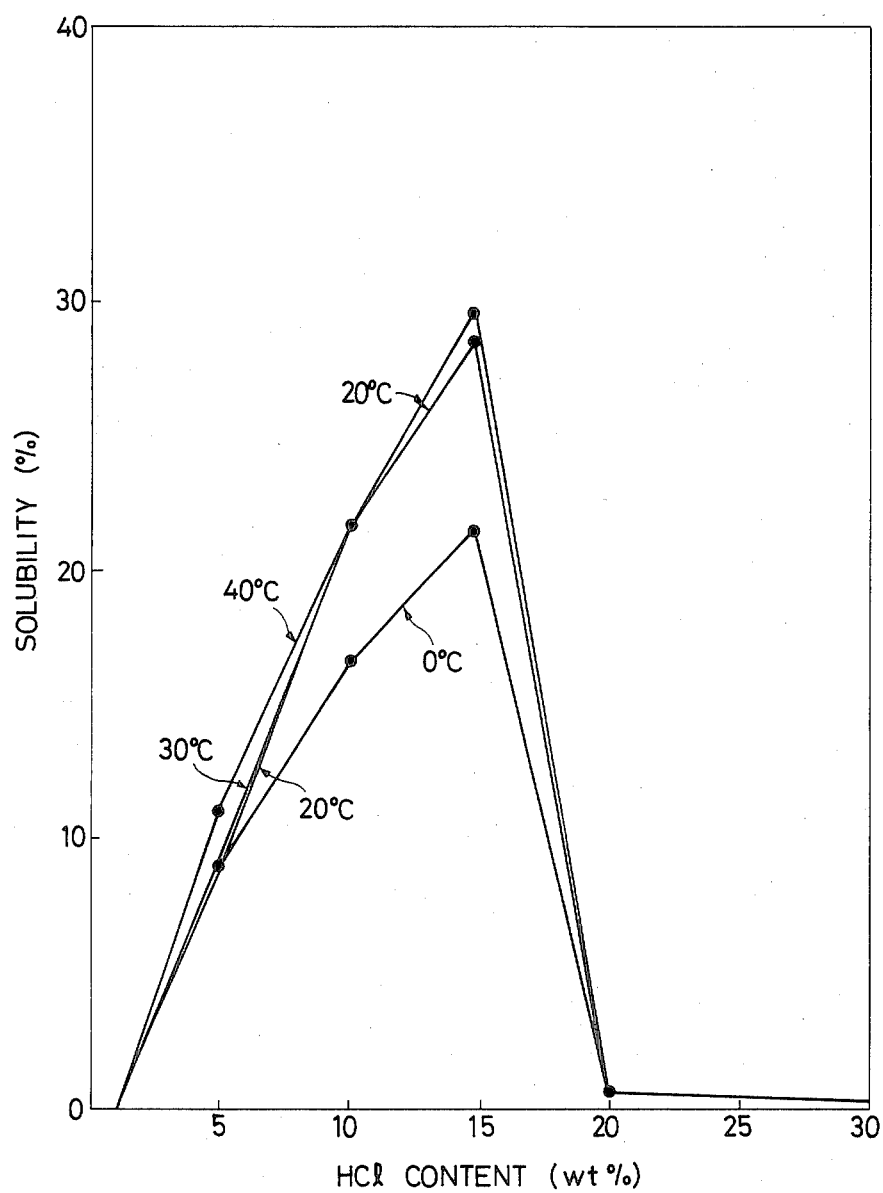
FIG. 2 is a graph showing the solubility of L-cystine in an aqueous solution in relation to its hydrochloric acid content at temperatures of 0° C., 20° C., 30° C. and 40° C., respectively.
Figure 3:
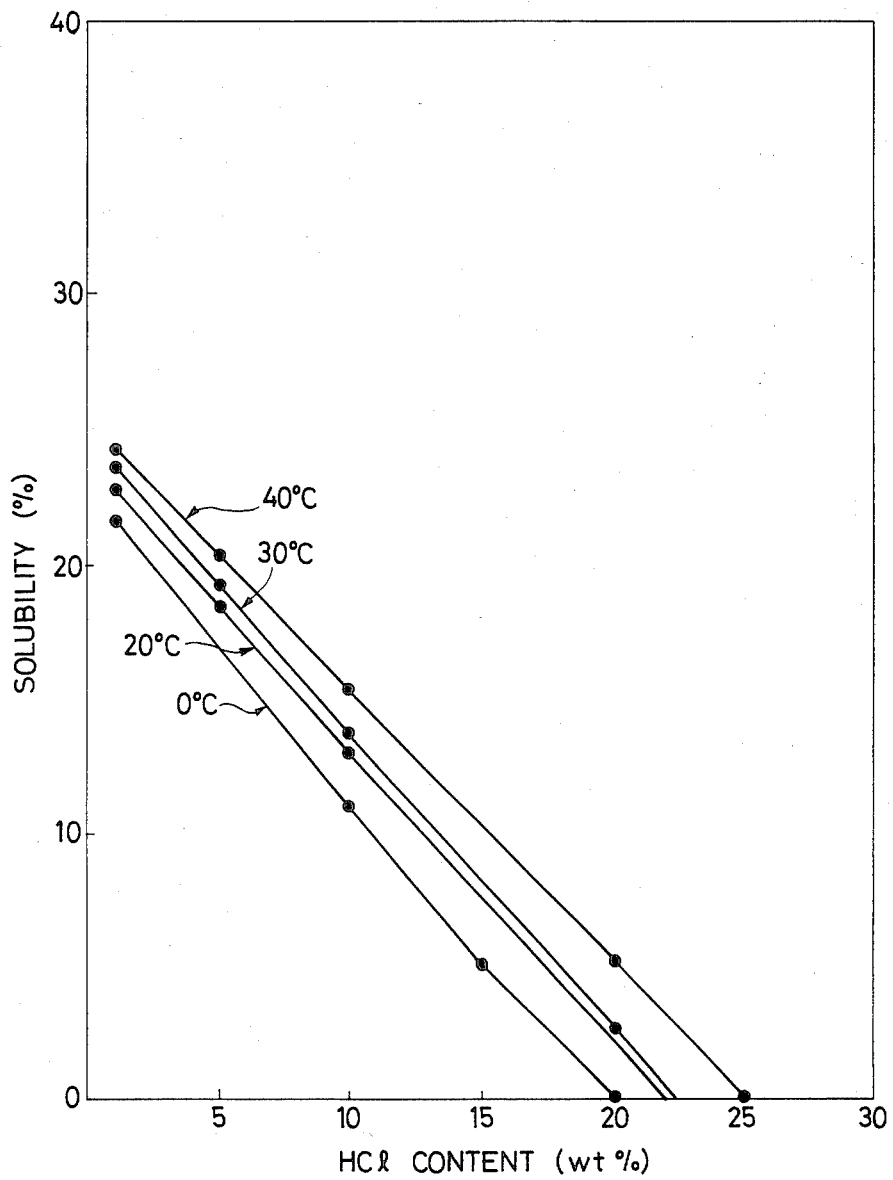
FIG. 3 is a graph showing the solubility of sodium chloride in an aqueous solution in relation to its hydrochloric acid content at temperatures of 0° C., 20° C., 30° C. and 40° C., respectively.
Figure 4:
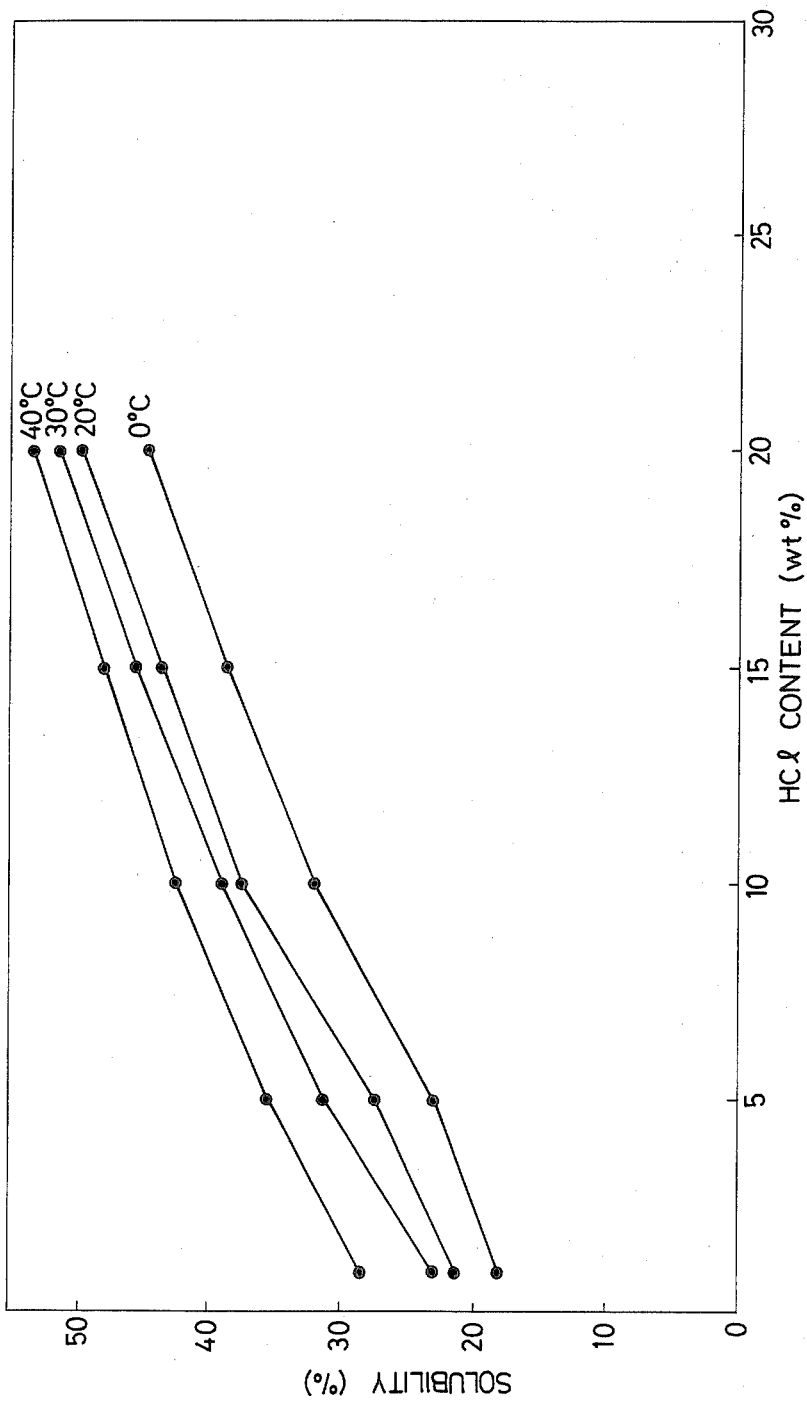
FIG. 4 is a graph showing the solubility of L-serine in an aqueous solution in relation to its hydrochloric acid content at temperatures of 0° C., 20° C., 30° C. and 40° C., respectively.

At a temperature of 20° C. or above, L-cysteine greatly increases its solubility in an aqueous solution containing about 15% by weight of hydrochloric acid and shows its maximum solubility in a solution containing about 20% by weight of hydrochloric acid, but sharply lowers its solubility in a solution having a higher content of hydrochloric acid, as shown in FIG. 1. Its solubility in a solution having a hydrochloric acid content exceeding 20% by weight shows a greater degree of dependence on the temperature. On the other hand, L-cystine and sodium chloride are hardly soluble in a solution having a hydrochloric acid content of about 20% by weight or more irrespective of the temperature, as shown in FIGS. 2 and 3. L-Serine proportionally increases its solubility in an aqueous solution containing hydrochloric acid with an increase in its hydrochloric acid content and temperature, as shown in FIG. 4.

According to the method of this invention, therefore, hydrochloric acid is added to a solution obtained by the reaction of L-serine until it contains at least 15% by weight of hydrochloric acid, and the solution is held at a temperature of at least 20° C., so that solids containing L-cystine and the inorganic salt may first be separated from the solution. Then, the solution is cooled to a temperature not exceeding 10° C. to form additional solids by crystallization, while L-serine is left in the solution, so that L-cysteine may be separated in the form of the monohydrate of its hydrochloride.

The reaction product of L-serine is preferably obtained by a method employing an enzyme, as it gives a high yield. When L-serine is reacted with a sulfhydryl compound in the presence of an enzyme to produce L-cysteine, a part of the L-cysteine which has been produced is converted to L-cystine nonenzymically by the action of dissolved oxygen, a metal employed as a source of the enzyme, etc. According to this invention, therefore, tryptophane synthase is, for example, used as the enzyme and hydrogen sulfide gas is used, instead of a metal sulfide or hydrosulfide, etc., to introduce a sulfhydryl group, so that a reducing atmosphere may be maintained throughout the reaction to prevent the formation of L-cystine as a byproduct.

When tryptophane synthase is employed, it is appropriate to maintain a pH of 7.5 to 9.0, but if hydrogen sulfide is used, it lowers the pH of the solution, as it is an acidic gas. Therefore, it is necessary to add an aqueous alkali solution appropriately to control the pH of the solution. Some alkalis, however, inhibit the enzyme reaction and prevent the satisfactory conversion of L-serine to L-cysteine. For example, ammonia inhibits the reaction greatly. Potassium hydroxide, potassium pyrophosphate and calcium hydroxide also inhibit the reaction and make it impossible to obtain the conversion of L-serine to L-cysteine which can be achieved when sodium hydroxide is employed. Therefore, it is advisable to use sodium hydroxide as the alkali for controlling the pH of the reactant solution.

Although there is no particular limitation to the amount of L-serine which the solution to be reacted may contain, it is usually preferable that it contain 1 to 2.5% by weight of L-serine.

There is no particular limitation to the amount of the enzyme which the solution may contain. It depends on various factors, such as the form of the enzyme which is employed, its activity and the amount of L-serine which the solution contains. It is advisable to add a very small amount of pyridoxal phosphate as a coenzyme so that the solution may contain 1 to 50 ppm thereof.

As regards the amount of hydrogen sulfide, it is preferable to use, say, 1.0 to 1.3 mols of hydrogen sulfide for each mol of L-serine. If too large an amount of hydrogen sulfide is employed, its loss by leakage increases. Moreover, an unduly large amount of sodium hydroxide must be used for controlling the pH of the solution and an undesirably large amount of sodium chloride is, therefore, formed. If too small an amount of hydrogen sulfide is used, no satisfactory reaction can be expected. Hydrogen sulfide is preferably blown into the solution for a period of, say, two to 12 hours.

The product of the enzyme reaction contains L-cysteine, L-cystine, sodium hydroxide, unreacted L-serine and the enzyme (bacteria). The bacteria which has been used as a source of the enzyme are removed from the reaction product. The bacteria are preferably removed before L-cysteine is separated from the reaction product. A customary method can be employed for removing the bacteria. Hydrochloric acid is added to the solution until it has a pH not exceeding 0.5 and the components other than the bacteria are dissolved. Then, an adsorbent, such as active carbon, is added in the quantity of 2 to 10% of L-cysteine and the solution is heated for a period of at least 30 minutes, so that the bacteria may be coagulated into flocs and separated from the solution.

When the bacteria have been removed, there is usually obtained a solution containing about 5 to 20% of L-cysteine, about 0.5 to 5% of L-cystine, about 0.5 to 5% of L-serine, about 3 to 15% of sodium chloride and about 3% of hydrochloric acid and having a pH value which is not higher than 0.5.

The solution is concentrated until its L-cysteine content is increased to about 25%. Hydrochloric acid gas is blown into the concentrated solution until it contains at least 15%, and preferably 20 to 30%, by weight of hydrochloric acid. If the solution contains only less than 15% by weight of hydrochloric acid, it is impossible to remove cystine and sodium chloride completely.

The blowing of hydrochloric acid gas into the solution is preferably carried out at a temperature of at least 20° C. Sodium chloride and L-cystine begin to be precipitated as the solution has a higher content of hydrochloric acid. The temperature of the solution is raised to about 70° C. by the heat of reaction which is generated when the gas is blown thereinto, but the solution can be left as it is. When the precipitated sodium chloride and L-cystine are separated from the solution, it is necessary to maintain it at a temperature of at least 20° C. and preferably from 30° C. to 40° C. Therefore, it is preferable to maintain the solution at a temperature of at least 20° C. even when hydrochloric acid gas is blown thereinto. If the temperature of the solution is lower than 20° C. when the sodium chloride and L-cystine are separated therefrom, there occurs a heavy loss of L-cysteine as the monohydrate of its hydrochloride is also precipitated. If the solution has too high a temperature, however, it is likely that the impurities which it contains may fail to be removed completely. The temperature at which the solution should be maintained when those impurities are separated therefrom must be selected by taking into account the amounts of hydrochloric acid and impurities which it contains.

After hydrochloric acid has been blown into the solution, it is held at the aforementioned temperature for at least half an hour so that sodium chloride and L-cystine may be solidified to form a cake. After the cake has been removed, the solution is cooled to a temperature not exceeding 10° C., and preferably a temperature between 10° C. and −15° C., so that the monohydrate of L-cysteine hydrochloride may be precipitated. The monohydrate, which is a white crystal, is separated from L-serine by filtration, while the L-serine is left in the solution.

Water is added to the cake of sodium chloride and L-cystine to dissolve sodium chloride, while L-cystine is recovered as a crystal.

As L-cysteine is relatively easily oxidized to form L-cystine, it is effective to provide a nitrogen gas seal or add a reducing agent to the solution in order to prevent the oxidation of L-cysteine.

The invention will now be described more specifically with reference to an example thereof. The known method of Gaitonde was employed for the analysis of cystine. The solution to be examined was diluted to 1000 to 2000 times by volume. A 5 μM solution of 1,4-dithiothreitol (reducing agent) was added to the diluted solution in a quantity approximately equal to that of the latter. A 2N solution of NaOH was added to the solution until it had a pH of 8.0 to 8.5, and the solution was left at room temperature for an hour so that all of the cystine which it contained might be reduced to cysteine. An acidic ninhydrin reagent was used to develop the color of cysteine and its absorbance was measured at 560 nm by an absorptiometer. The concentration of cysteine and cystine in the solution to be examined was calculated in accordance with a working curve which had been prepared to show the absorbance at 560 nm of a standard sample having a known concentration. The concentration of cysteine was calculated without reduction by 1,4-dithiothreitol. The concentration of cystine was obtained by deducting the concentration of cysteine from the concentration of cysteine and cystine.

EXAMPLE

A 200 ml separable flask which was provided with a stirrer, a blowing tube and an exhaust pipe was charged with 10 g of L-serine and 2.5 mg of pyridoxal phosphate. Water of ion exchange was added to prepare 100 g of a solution. A 32% solution of NaOH was added to the reactant solution until it had a pH of 8.0. Then, the flask was charged with 2.0 g (dry weight) of bacteria containing tryptophane synthase, i.e. *Escherichia coli* MT-10242 (FERM BP-20), while the solution was maintained at a temperature of 45° C. Hydrogen sulfide gas was blown into the solution at a rate of about 10 ml per minute. The blowing of the gas was continued for about four hours. About 1.1 mols of hydrogen sulfide were used for each mol of L-serine. Then, the solution was stirred for two hours to complete its reaction. During its reaction, a 32% solution of NaOH was added to maintain the reaction system at a pH of 8.0. A total of about 15 g of the NaOH solution, including the amount used for the initial pH control, was consumed.

A reaction product weighing 113 g was obtained. A sample of the product was dissolved in a 2N solution of hydrochloric acid and the bacteria were removed therefrom by centrifugal separation. It was analyzed for L-cysteine and L-cystine. It was found to contain 8.56% of L-cysteine and 0.50% of L-cystine. These values represented a conversion rate of 84.0% and 5.0%, respectively, from L-serine.

18.2 g of a 35% solution of hydrochloric acid was added to the reaction product under stirring so that it might have a pH of 0.5. After 1.0 g of active carbon had been added, the solution was heated at 90° C. for an hour under stirring. The hot solution was subjected to vacuum filtration by a Nutsche, whereby the bacteria were removed therefrom.

Then, the solution was concentrated to a weight of 45 g and while the solution was held at a temperature of 40° C., dry hydrochloric acid gas was blown into the solution until it had a weight of 53 g containing 8 g (about 18.9% by weight) of hydrochloric acid. The solution was held at 40° C. for another hour under stirring. Then, it was subjected to vacuum filtration by a Nutsche, whereby a mixed cake of sodium chloride and L-cystine was separated from the solution. The cake had a wet weight of 7.6 g.

Then, the solution was cooled to a temperature of −10° C. and held at that temperature for two hours, whereby the monohydrate of L-cysteine hydrochloride was obtained as a white crystal. It was separated from the solution by vacuum filtration and had a weight of 9.3 g. This value represented the recovery of 62.0 mol % of L-serine.

The product had a purity of 99.6%, an ash content of 0.02% and a $[\alpha]_D^{20}$ value of +6.5. It did not contain any other amino acid, but was a product satisfying the requirements of JIS.

The mixed cake was dissolved in 20 ml of water. Sodium hydroxide was added to the solution until it had a pH of about 3, whereby a white crystal of L-cystine was formed. It was collected by filtration, washed and dried to yield 0.9 g of L-cystine.

What is claimed is:

1. A method of separating L-cysteine from a solution containing L-cysteine, L-cystine, L-serine and an inorganic salt, comprising:
   adding hydrochloric acid to said solution until it contains at least 15% by weight of hydrochloric acid;
   holding said solution at a temperature of at least 20° C. to separate a solid containing said L-cystine and said salt from said solution;
   cooling said solution to a temperature not higher than 10° C. to allow crystallization to form the monohydrate of L-cysteine hydrochloride; and
   separating said monohydrate from said L-serine in said solution.

2. A method as set forth in claim 1, wherein hydrochloric acid is added until said solution contains 20 to 30% by weight of hydrochloric acid.

3. A method as set forth in claim 1, wherein said solution has a temperature of 30° C. to 40° C. when said solid is separated therefrom.

4. A method as set forth in claim 1, wherein said solution is a product of an enzyme reaction which has been obtained by employing hydrogen sulfide gas as an agent for introducing a sulfhydryl group.

5. A method as set forth in claim 1, wherein said inorganic salt is sodium chloride.

* * * * *